US008693701B2

(12) United States Patent
Scarlett et al.

(10) Patent No.: US 8,693,701 B2
(45) Date of Patent: Apr. 8, 2014

(54) AUDIO DEVICE

(75) Inventors: Shawn Scarlett, Nijmegen (NL); Jan-Paul Paulus Huijser, Wychen (NL)

(73) Assignee: NXP B.V., Eindhoven (NL)

( * ) Notice: Subject to any disclaimer, the term of this patent is extended or adjusted under 35 U.S.C. 154(b) by 421 days.

(21) Appl. No.: 13/157,112

(22) Filed: Jun. 9, 2011

(65) Prior Publication Data

US 2012/0148062 A1 Jun. 14, 2012

(30) Foreign Application Priority Data

Jun. 11, 2010 (EP) .................................... 10165752

(51) Int. Cl.
*A61F 11/06* (2006.01)
*H04R 1/10* (2006.01)

(52) U.S. Cl.
USPC ............................ 381/71.6; 361/74; 361/71.1

(58) Field of Classification Search
USPC ............ 381/71.6, 74, 75, 58, 71.1–71.12, 93, 381/94, 194.9
See application file for complete search history.

(56) References Cited

U.S. PATENT DOCUMENTS 7,270,554 B2 9/2007 Corey et al.
7,349,546 B2 * 3/2008 Ganton ........................... 381/58
8,223,986 B2 * 7/2012 Sander et al. ................... 381/74
2008/0175402 A1 7/2008 Abe et al.
2009/0180629 A1 * 7/2009 Sander et al. ................... 381/58
2009/0245529 A1 10/2009 Asada et al.

FOREIGN PATENT DOCUMENTS

EP 1 242 992 B1 3/2006

OTHER PUBLICATIONS

Extended European Search Report for European Patent Appln. No. 10165752.6 (Nov. 22, 2010).

* cited by examiner

*Primary Examiner* — Vivian Chin
*Assistant Examiner* — Ammar Hamid

(57) ABSTRACT

Existing ANC headsets have active noise reduction circuitry and a power supply in the headset. Alternate ANC headsets rely on ANC circuitry in the player and have non-standard connectors meaning that they cannot be used with any other players. An audio headset (90) having an encoder (54) and active noise cancellation audio processing device (80) having a decoder (32) are described. The encoder (54) enables the audio headset to be used in enhanced (ANC) mode when connected to a compatible audio processing device and in normal mode when connected to a non-compatible audio processing device since a standard audio jack plug can be used. Similarly the decoder (62) in the active noise cancellation audio processing device (80) enables the active noise cancellation audio processing device to be used in enhanced mode when connected to a compatible audio headset and in normal mode connected to a non-compatible audio headset since a standard audio socket can be used.

15 Claims, 3 Drawing Sheets

AUDIO DEVICE

CROSS-REFERENCE TO RELATED APPLICATIONS

This application claims the priority under 35 U.S.C. §119 of European patent application no. 10165752.6, filed on Jun. 11, 2010, the contents of which are incorporated by reference herein.

FIELD OF THE INVENTION

The present invention relates to audio headsets compatible with active noise cancelling audio processing devices and audio processing devices without noise cancelling. It further relates to active noise cancelling audio processing devices and active noise cancelling audio systems comprising audio headsets and audio processing devices.

BACKGROUND OF THE INVENTION

It is known that active noise cancellation (ANC) is a feature in audio headsets. Currently for most systems with ANC functions, the active circuitry is built into the headset along with a power source. The headset has a pair of microphones located close to each ear to sample the noise that is to be cancelled; those signals are processed in the headset and an anti-noise signal is generated. The anti-noise signal and the playback signal coming from the player are then the mixed and amplified to the earpiece.

The entire active headset is then connected to the audio device typically using a 3.5 mm jack. Cell phones, audio players and other headset devices generally use a 3.5 mM audio plug and socket for providing audio output to headphones or analogue interconnection with other audio devices. Headsets typically use a 3-connector system for stereo audio or mono audio and a microphone, and a 4-connector system for headsets with stereo output and a microphone input.

Alternatively, the ANC circuitry can be built into the audio processing device itself. This has the advantage of allowing the headset to operate without a battery and it reduces the cost of a headset. A problem with this approach is that is requires additional mechanical connections to pass the noise signals, from the headset to the audio device. Currently unique mechanical designs are used to enable those systems to be interoperable with standard headphones. However, this results in a system where only one side of the device/headset pair is compatible with standard equipment.

U.S. Pat. No. 7,270,554 uses additional mechanical connectors that are combined with a single standard stereo headphone connector. This enables a standard headset to be used with the audio device, but requires additional mechanical connectors for the ANC functions.

Sony uses a similar approach in its noise cancelling Walkman™ players by adding a unique mechanical connection on its headset, the receiving socket can be configured to allow for both the ANC version and standard headsets. However the Sony headset cannot be used with other audio players.

Therefore there is a need to develop a cheap audio headset that is compatible with standard connectors.

SUMMARY OF THE INVENTION

According to a first aspect of the invention, there is provided an audio headset compatible with active noise cancelling audio processing devices and audio processing devices without active noise cancelling, the audio headset comprising: at least one microphone for measuring noise; an encoder for encoding a noise measurement signal received from the microphone via an input of the encoder, to produce an encoded noise measurement signal; and a connector for connecting the audio headset to an audio processing device, the connector having a terminal for carrying a microphone signal, wherein the audio headset is operable when connected to an active noise cancelling audio processing device: to output the encoded noise measurement signal via the terminal, and to receive a combined audio and anti-noise signal from the active noise cancelling audio processing device; and when connected to an audio processing device without active noise cancelling: to output either a null signal or an unencoded signal from the at least one microphone via the terminal; and to receive an audio signal from the audio processing device without active noise cancelling.

By encoding the noise measurement signal, it is possible to have multiple microphone signals on a single connection between a headset and an audio processing device. This allows, for example, the standard microphone signal connector on a 3.5 mm connector to be used with ANC headsets having 2 or more microphones, when connected to an active noise cancelling audio processing device.

In addition, by passing either a standard microphone signal or null signal and receiving an audio signal when connected to either an audio processing device without active noise cancellation or an audio processing device without a compatible decoder, the headset can be used with other audio devices. This is because the headset can maintain standard passive connections between the jack and the earpiece drivers (stereo or mono) when no microphone bias is provided, or when only a standard microphone bias is applied. In cases where a microphone is present it can also provide a standard microphone signal output.

According to an embodiment of the invention, the power supply for the encoder is supplied via the terminal. The terminal carries a bias voltage for a microphone on the headset, so using this bias to power the encoder means that no separate power supply for the headset is required, and the power supply for the headset be connected using a standard audio connector.

According to a further embodiment of the invention, the audio headset comprises at least one switch coupled to a further input of the encoder, wherein the audio headset is operable to output a signal comprising the state of the at least one switch and the encoded microphone signals. This allows multiple switches or buttons to be located on the headset for controlling different functions. These can then be encoded along with noise measurement signals and other microphone signals and sent to an audio processing device. It also allows higher current limits to be used for a microphone input line, as if the button or switch is directly in the microphone line, the standard call/release button function on a headset used for a mobile phone may not function.

In a second aspect of the invention, there is provided an active noise cancelling audio processing device comprising a connector for connecting the audio processing device to an audio headset, the connector having a terminal for carrying a microphone signal, an active noise cancelling processor, a decoder having an input coupled to the terminal and an output coupled to the active noise cancelling processor; wherein the audio processing device is operable when connected to an audio headset adapted for active noise cancellation to receive an encoded noise measurement signal from the audio headset via the terminal, to use the decoder to decode the encoded noise measurement signal, and to use the active noise cancelling processor to generate a combined audio and anti-noise signal, and when connected to a audio headset not adapted for active noise cancelling to receive an unencoded microphone signal or null signal from the audio headset via the terminal, and to generate an audio signal not including an anti-noise signal.

The decoder can be used to decode signals from, for example, multiple microphones in a headset, and so only one terminal is required for more than one microphone. This can allow a standard connector to be used when connecting the audio processing device to a compatible headset which is adapted for noise cancellation and has a corresponding encoder.

Furthermore, because the audio processing device is also operable to receive unencoded microphone signals or null signals and to generate an audio signal without any noise cancellation, the audio processing device can also be used with other audio headsets.

In a further aspect of the invention, there is provided an active noise cancellation system comprising the audio headset of any of claims 1 to 8 connectable to the active noise cancelling audio processing device of any of claims 9 to 12 by means of their respective connectors.

The noise reduction signal encoding and decoding allows enhanced communication between the headset and the audio processing device so enabling active noise cancellation with standard connectors so that either component can be used with other equipment. Furthermore, the active noise reduction processing circuitry for the system is located in the audio processing device, reducing the cost of the headset.

BRIEF DESCRIPTION OF THE DRAWINGS

Embodiments of the invention are now described by way of example with reference to the accompanying drawings in which.

DETAILED DESCRIPTION OF THE INVENTION

Figure 1:
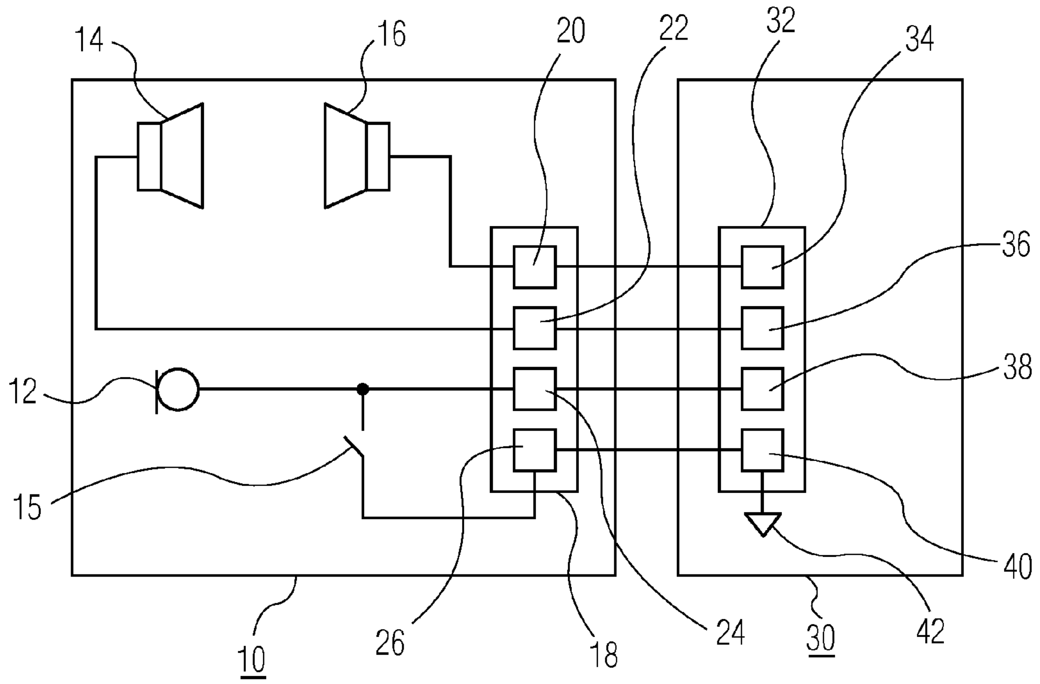
FIG. 1 PRIOR ART
FIG. 1 illustrates an example of a known audio headset and an audio processing device.

FIG. 1 illustrates an example of a known audio processing system consisting of an audio headset 10 connected to an audio processing device 30. A headset 10 has a microphone 12 adapted for speech, a first headphone or earpiece 14, a second headphone or earpiece 16, a connector 18 for connecting to an audio processing device. The connector can have a first headphone terminal 22, a second headphone terminal 20, a microphone terminal 24, and a ground reference terminal 26. The connecter can be a 3.5 mm audio jack according to the open mobile terminal platform standard. The switch is connected between microphone 12 and ground reference terminal 26. Microphone 12 is connected to microphone terminal 24. The first headphone 14 is connected to the first microphone terminal 22. The second headphone 16 is connected to the second microphone terminal 20.

An audio processing device 30 such as a mobile phone, mp3 player or other audio playing device has a connecter 32 which can be a 3.5 mm socket. The connector has a first headphone terminal 36, a second headphone terminal 34, a microphone terminal 38, and a ground reference terminal 40. The ground reference terminal can be connected to a ground reference 42. The audio processing device 30 provides audio signals to the first headphone terminal 36, and second headphone terminal 34. The audio processing device 30 can receive a microphone input signal on microphone terminal 38. The audio processing device can also supply a microphone bias voltage to microphone terminal 38.

The audio processing device 30 is connected to the headset 10 by means of the connectors 18, 32.

Figure 2:
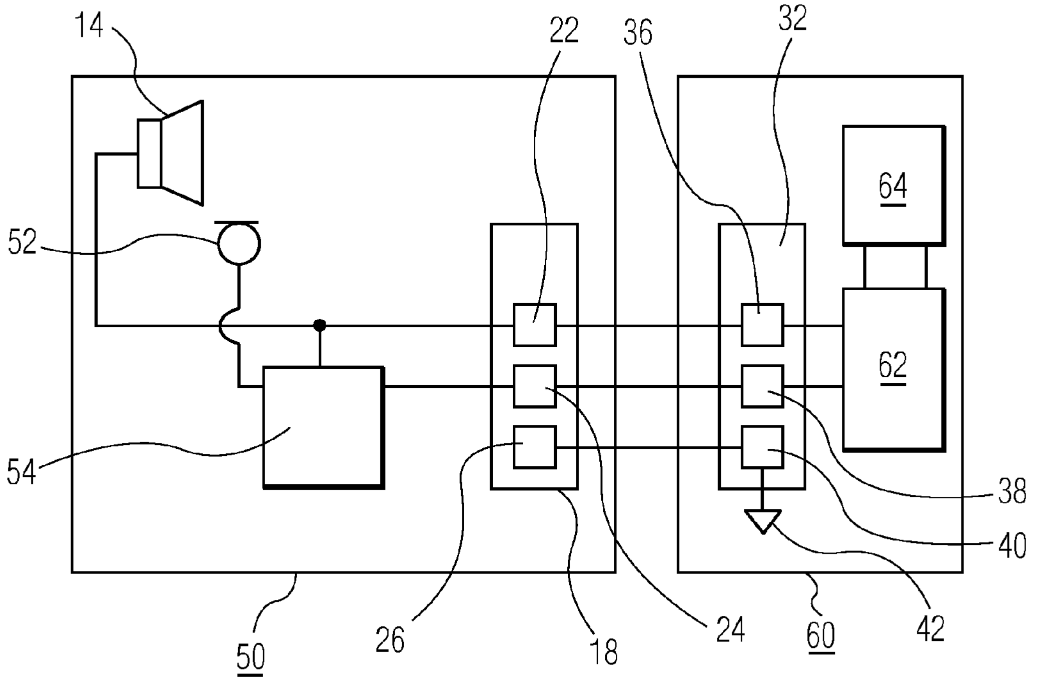
FIG. 2 shows an audio headset adapted for active noise cancellation and an active noise cancelling audio processing device according to a first embodiment of the invention.

FIG. 2 shows an active noise cancellation system with an audio headset 50 according to an embodiment of the invention and an active noise cancelling audio processing device 60 according to a further embodiment of the invention.

Audio headset 50 can have headphone or earpiece 14, a microphone 52 which can be adapted to detect ambient noise, an encoder 54, a connector 18 which can have a headphone terminal 22, a microphone terminal 24 and a ground reference terminal 26. The connector 18 may be a 3.5 mm audio jack plug. Microphone 52 can be coupled to an input of the encoder 54. An input or an output of the encoder 54 can be connected to microphone terminal 24. A further input of the encoder 54 can be connected to a headphone terminal 22. The headphone terminal 22 can be connected to the headphone 14. The encoder 54 can provide an audio headset identifier signal to the microphone terminal. The frequency of the audio headset identifier signal can be outside the audible frequency. Audio processing device 60 can have a connector 32, a decoder 62, and an active noise processing circuit 64. The connector can have a headphone terminal 36, a microphone terminal 38 and a ground reference terminal 40. The decoder can be connected to the headphone terminal 36 and the microphone terminal 38. The decoder 62 can provide an audio processing device identifier signal to the headphone terminal. The audio processing device identifier signal can be a signal that is outside the audible frequency. The audio headset 50 and audio processing device 60 can be connected together by means of connectors 22 and 32.

In operation the active noise cancellation system can work as follows. On initial power up, the decoder 62 can provide an audio processing device identifier signal which can be received by the encoder 54, and the encoder 54 provides an audio headset identifier signal which can be received by the decoder 62.

The encoder 62 can receive an audio processing device identifier signal; this can indicate a compatible audio processing device. The encoder can encode ambient noise detected by microphone 52. The encoded ambient noise can be decoded by decoder 62 and the decoded microphone signal can be routed to the active noise processor 64. The active noise processor can generate an anti-noise signal from the decoded microphone signal which is mixed with the desired audio signal. This combined anti-noise and audio signal can then be routed to the headphone terminal 36 in the active noise cancelling audio processing device 60 which is connected to terminal 22 in the audio headset 50.

In some embodiments, the power supply for the encoder 54 can be provided by the audio processing device by adapting the bias voltage and current provided on the microphone terminal 38.

In further embodiments, the audio processing device can be a mobile phone, a smart phone or other audio processing devices such as MP3 player, TV or Computer.

Figure 3:
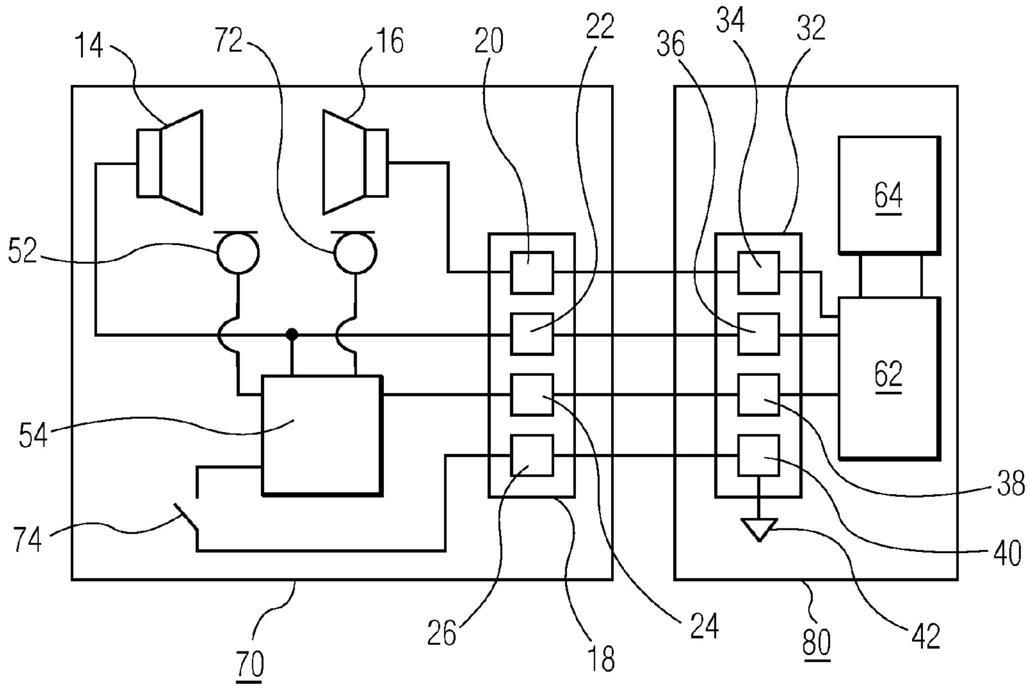
FIG. 3 illustrates an audio headset adapted for active noise cancellation and an active noise cancelling audio processing device according to a further embodiment of the invention.

FIG. 3 shows a further embodiment of an active noise cancellation system with an audio headset 70 and an active noise cancelling audio processing device 80. Audio headset 70 can have headphone or earpiece 14, a microphone 52 which can be adapted to detect ambient noise, a second microphone 72 which can be adapted to detect ambient noise, an encoder 54, a switch 74, a connector 18 which can have a first headphone terminal 22, a second headphone terminal 20, a microphone terminal 24 and a ground reference terminal 26. The connector 18 may be a 3.5 mm audio jack plug. Microphone 52 can be coupled to an input of the encoder 54. Second microphone 72 can be coupled to a further input of the encoder 54. An input or an output of the encoder 54 can be connected to microphone terminal 24. A further input of the encoder 54 can be connected to a headphone terminal 22. The headphone terminal 22 can be connected to the first headphone 14. Switch 74 can be coupled to an input of the encoder 54 and ground reference terminal 26. The encoder 54 can provide an audio headset identifier signal to the microphone terminal. The frequency of the audio headset identifier signal can be outside the audible frequency.

Audio processing device 60 can have a connector 32, a decoder 62, and an active noise processing circuit 64. The connector can have a first headphone terminal 36, a second headphone terminal 34, a microphone terminal 38 and a ground reference terminal 40. The decoder can be connected to the first and second headphone terminals 34, 36 and the microphone terminal 38. The decoder 62 can provide an audio processing device identifier signal to the first headphone terminal 36. The audio processing device identifier signal can be a signal that is outside the audible frequency.

The audio headset 50 and audio processing device 60 can be connected together by means of connectors 22 and 32.

In operation the active noise cancellation system can work as follows. On initial power up, the decoder 62 can provide an audio processing device identifier signal which can be received by the encoder 54, and the encoder 54 provides an audio headset identifier signal which can be received by the decoder 62.

The encoder 62 can receive an audio processing device identifier signal; this can indicate a compatible audio processing device. The encoder can encode ambient noise detected by microphones 52 and 72 and the state of the switch 74. The encoded ambient noise can be decoded by decoder 62 and the decoded microphone signals from the microphones 52 and 72 can be routed to the active noise processor 64. The active noise processor 80 can generate an anti-noise signal from the decoded microphone signal which is mixed with the desired audio signal. This combined anti-noise and audio signal can then be routed to the headphone terminal 36 in the active noise cancelling audio processing device 80 which is connected to terminal 22 in the audio headset 70. The decoded state of the switch 74 can be routed to the active noise cancellation processor 64.

In some embodiments the encoding scheme used can be amplitude modulation with different carrier frequencies being used for first microphone 52, second microphone 72, and state of switch 74.

In other embodiments different inputs to the encoder can be sampled at different times. This can require the decoder 62 to provide a clock signal on the headphone terminal 36 which can be received at an input of the encoder 54. The frequency of the clock can be greater than the audible frequency, i.e. a higher frequency than 20 KHz.

Figure 4:
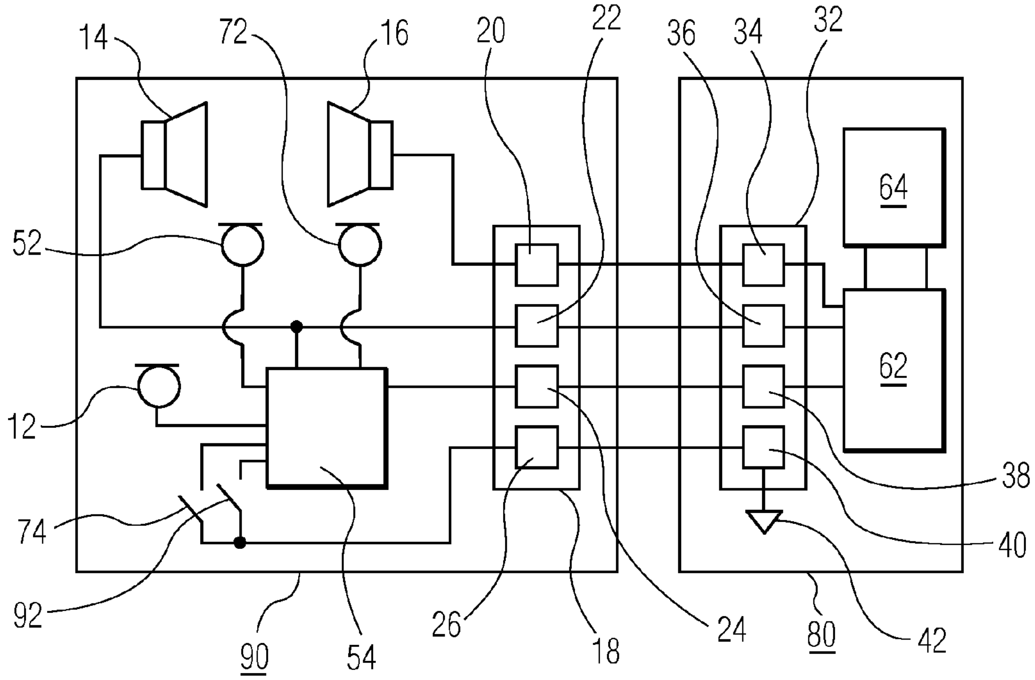
FIG. 4 shows an audio headset adapted for active noise cancellation and an active noise cancelling audio processing device according to another embodiment of the invention.

FIG. 4 shows a further embodiment of an active noise cancellation system with an audio headset 90 and an active noise cancelling audio processing device 80. Audio headset 90 can have headphone or earpiece 14, a microphone 52 which can be adapted to detect ambient noise, a second microphone 72 which can be adapted to detect ambient noise, an encoder 54, a switch 74, a further switch 92, a connector 18 which can have a first headphone terminal 22, a second headphone terminal 20, a microphone terminal 24 and a ground reference terminal 26. The connector 18 may be a 3.5 mm audio jack plug. Microphone 52 can be coupled to an input of the encoder 54. Second microphone 72 can be coupled to a further input of the encoder 54. An input or an output of the encoder 54 can be connected to microphone terminal 24. A further input of the encoder 54 can be connected to a headphone terminal 22. The headphone terminal 22 can be connected to the first headphone 14. Switch 74 can be coupled to an input of the encoder 54 and ground reference terminal 26. Further switch 92 can be coupled to an input of the encoder 54 and ground reference terminal 26. The encoder 54 can provide an audio headset identifier signal to the microphone terminal. The frequency of the audio headset identifier signal can be outside the audible frequency.

Audio processing device 80 can have a connector 32, a decoder 62, and an active noise cancelling processing circuit 64. The connector can have a first headphone terminal 36, a second headphone terminal 34, a microphone terminal 38 and a ground reference terminal 40. The decoder can be connected to the first and second headphone terminals 34, 36 and the microphone terminal 38. The decoder 62 can provide an audio processing device identifier signal to the first headphone terminal 36. The audio processing device identifier signal can be a signal that is outside the audible frequency range. The audio headset 50 and audio processing device 60 can be connected together by means of connectors 22 and 32.

In operation the active noise cancellation system can work as follows. On initial power up, the decoder 62 can provide an audio processing device identifier signal which can be received by the encoder 54, and the encoder 54 provides an audio headset identifier signal which can be received by the decoder 62. The encoder 62 can receive an audio processing device identifier signal; this can indicate a compatible audio processing device. The encoder can encode ambient noise detected by microphones 52 and 72 and the states of the switch 74 and further switch 92. The encoded ambient noise can be decoded by decoder 62 and the decoded microphone signals from the microphones 52 and 72 can be routed to the active noise processor 64. The active noise processor 80 can generate an anti-noise signal from the decoded microphone signal which is mixed with the desired audio signal. This combined anti-noise and audio signal can then be routed to the headphone terminal 36 in the active noise cancelling audio processing device 80 which is connected to terminal 22 in the audio headset 90. The decoded state of the switch 74 further switch 92 can be routed to the active noise cancellation processor 64.

In other embodiments, the decoded state of the switch 74 further switch 92 can be routed to other circuitry within the audio processing device. In further embodiments switch 74 can be a call-end button for a mobile phone. In other embodiments switch 92 can be used to switch encoder 54 between encode and non-encode function.

Figure 5:
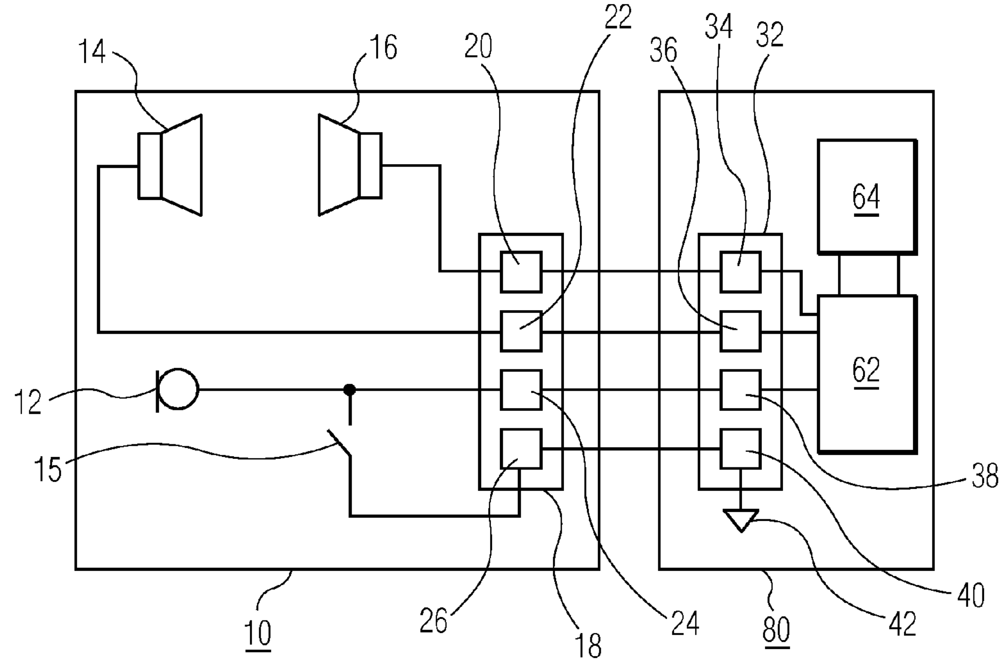
FIG. 5 shows an example of a known audio headset and an active noise cancelling audio processing device according to another embodiment of the invention.

FIG. 5 shows an audio system having a non-compatible audio headset 10 connected to an active noise cancellation audio processing device 80. A headset 10 has a microphone 12 adapted for speech, a first headphone or earpiece 14, a second headphone or earpiece 16, a connector 18 for connecting to an audio processing device. The connector can have a first headphone terminal 22, a second headphone terminal 20, a microphone terminal 24, and a ground reference terminal 26. The connecter can be a 3.5 mm audio jack. The switch is connected between microphone 12 and ground reference terminal 26. Microphone 12 is connected to microphone terminal 24. The first headphone 14 is connected to the first microphone terminal 22. The second headphone 16 is connected to the second microphone terminal 20.

Audio processing device 80 can have a connector 32, a decoder 62, and an active noise cancelling processor circuit 64. The connector can have a first headphone terminal 36, a second headphone terminal 34, a microphone terminal 38 and a ground reference terminal 40. The decoder can be connected to the first and second headphone terminals 34, 36 and the microphone terminal 38. The decoder 62 can provide an audio processing device identifier signal to the first headphone terminal 36. The audio processing device identifier signal can be a signal that is outside the audible frequency.

The audio headset 10 and audio processing device 80 can be connected together by means of connectors 22 and 32. In operation, on initial power up the audio processing device does not receive an audio headset initialization signal from audio headset 10. The decoder 62 routes the unencoded microphone signals received on terminal 38 to other circuitry in the audio processing device. In other embodiments, the audio processing device can have a switch to manually switch between decode and non-decode operation of the decoder.

Figure 6:
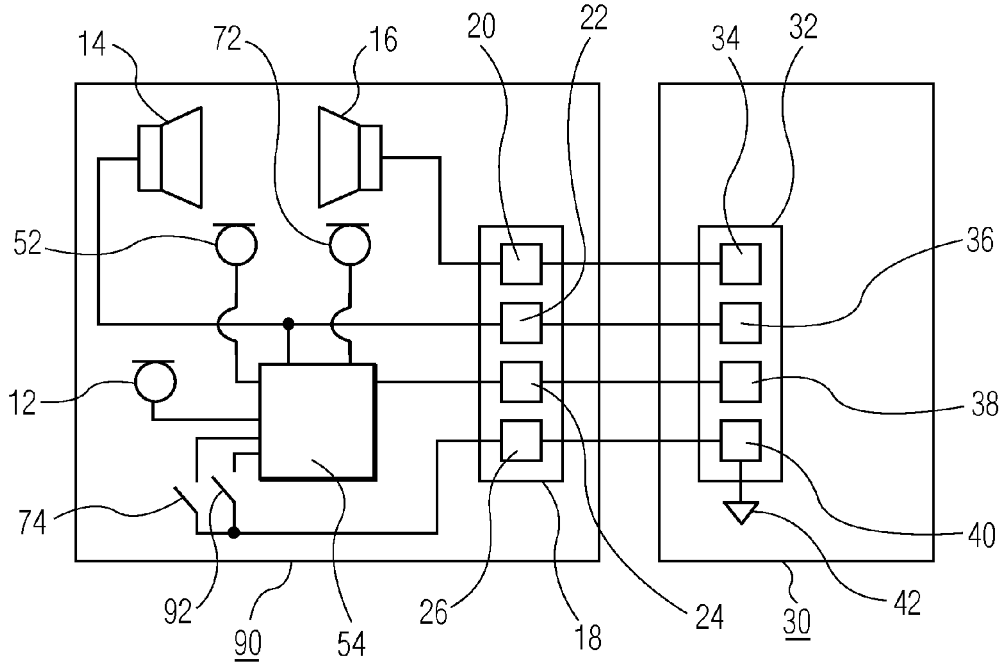
FIG. 6 illustrates an example of an audio headset adapted for active noise cancellation and a known audio processing device according to a further embodiment of the invention.

FIG. 6 shows an audio headset adapted for active noise cancellation 90 connected to a non-compatible audio processing device 30. Audio headset 90 can have headphone or earpiece 14, a microphone 52 which can be adapted to detect ambient noise, a second microphone 72 which can be adapted to detect ambient noise, an encoder 54, a switch 74, a further switch 92, a connector 18 which can have a first headphone terminal 22, a second headphone terminal 20, a microphone terminal 24 and a ground reference terminal 26. The connector 18 may be a 3.5 mm audio jack plug. Microphone 52 can be coupled to an input of the encoder 54. Second microphone 72 can be coupled to a further input of the encoder 54. An input or an output of the encoder 54 can be connected to microphone terminal 24. A further input of the encoder 54 can be connected to a headphone terminal 22. The headphone terminal 22 can be connected to the first headphone 14. Switch 74 can be coupled to an input of the encoder 54 and ground reference terminal 26. Further switch 92 can be coupled to an input of the encoder 54 and ground reference terminal 26. The encoder 54 can provide an audio headset identifier signal to the microphone terminal. The frequency of the audio headset identifier signal can be outside the audible frequency.

An audio processing device 30 such as a mobile phone, mp3 player or other audio playing device has a connecter 32 which can be a 3.5 mm socket. The connector has a first headphone terminal 36, a second headphone terminal 34, a microphone terminal 38, and a ground reference terminal 40. The ground reference terminal can be connected to a ground reference 42. The audio processing device 30 provides audio signals to the first headphone terminal 36, and second headphone terminal 34. The audio processing device 30 can receive a microphone input signal on microphone terminal 38. The audio processing device can also supply a microphone bias voltage to microphone terminal 38. The audio processing device 30 is connected to the audio headset 90 by means of the connectors 18, 32.

On power up the audio headset 90 may not receive an audio processing device identifier signal. The decoder 54 can route the unencoded microphone signal 12 to microphone terminal 24. The decoder can couple the switch 74 to microphone 12.

In other embodiments a further switch on the audio headset 90 can switch the encoder between encode and non-encode function. In further embodiments, the encoder for the audio headset can be integrated into the microphone pre-amplifier circuit. In some embodiments of the audio headset, other switches or buttons coupled to the encoder can be provided for other functions; for example to switch between ANC and non-ANC mode. In other embodiments further microphones can be added to the headset to enable multi-microphone anti-noise reduction.

In other embodiments, the active noise cancellation audio processing device 80 can modify the power supply to a higher voltage and/or current when the connection to audio headset 90 is detected. In further embodiments of active noise cancellation audio processing device 80, the decoder 62 can be integrated with a headphone amplifier.

There is described an audio headset 90 having an encoder 54 and active noise cancellation audio processing device 80 having a decoder 62. The encoder 54 enables the audio headset to be used in enhanced (ANC) mode when connected to a compatible audio processing device and in normal mode when connected to a non-compatible audio processing device since a standard audio jack plug can be used. Similarly the decoder 62 in the active noise cancellation audio processing device 80 enables the active noise cancellation audio processing device to be used in enhanced mode when connected to a compatible audio headset and in normal mode connected to a non-compatible audio headset, since a standard audio socket can be used.

The invention claimed is:

1. An audio headset compatible with active noise cancelling audio processing devices and audio processing devices without active noise cancelling, the audio headset comprising:

at least one microphone for measuring noise;

an encoder for encoding a noise measurement signal received from the microphone via an input of the encoder, to produce an encoded noise measurement signal; and a connector for connecting the audio headset to an audio processing device, the connector having a terminal for carrying a microphone signal, wherein the audio headset is configured to detect if a device to which the audio headset is connected to is an active noise cancelling audio processing device or an audio processing device without active noise cancelling, wherein the audio headset is operable when connected to the active noise cancelling audio processing device to output the encoded noise measurement signal via the terminal and to receive a combined audio and anti-noise signal from the active noise cancelling audio processing device; and when connected to the audio processing device without active noise cancelling:

to output one of a null signal and an unencoded signal from the at least one microphone via the terminal; and to receive an audio signal from the audio processing device without active noise cancelling.

2. The audio headset of claim 1, further comprising at least one switch coupled to a further input of the encoder, and wherein the audio headset is operable to output an encoded signal reflecting a state of the at least one switch and the encoded microphone signals.

3. The audio headset according to claim 1, wherein a power supply for the encoder is supplied via the terminal.

4. The audio headset according to claim 1, wherein the connector comprises a 3.5 mm audio plug.

5. The audio headset according to claim 1, wherein the connector comprises a further terminal for receiving an identifying signal for identifying a compatible active noise cancelling audio processing device, and the encoder comprises a further input coupled to the further terminal, wherein the encoder is operable to receive the identifying signal via the further terminal and enable or disable encoding according to a content of the identifying signal.

6. The audio headset of claim 1, wherein the encoder is operable to send an audio headset identifying signal via the terminal of the connector.

7. The audio headset of claim 6 wherein the audio headset identifying signal has a frequency greater than 20 KHz.

8. The audio headset of claim 6 wherein the audio headset identifying signal includes audio headset calibration parameters.

9. An active noise cancelling audio processing device comprising a connector for connecting the audio processing device to an audio headset, the connector having a terminal for carrying a microphone signal, an active noise cancelling processor, a decoder having an input coupled to the terminal and an output coupled to the active noise cancelling processor; wherein the audio processing device is operable when connected to an audio headset adapted for active noise cancellation to receive an encoded noise measurement signal from the audio headset via the terminal;

to use the decoder to decode the encoded noise measurement signal; and to use the active noise cancelling processor to generate a combined audio and anti-noise signal; and when connected to an audio headset not adapted for active noise cancelling:

to receive one of an unencoded microphone signal and a null signal from the audio headset via the terminal; and to generate an audio signal not including an anti-noise signal, wherein the audio processing device is configured to provide a notification to the audio headset to enable the audio headset to determine if the audio processing device includes the active noise cancelling processor.

10. The active noise cancelling audio processing device of claim 9, wherein the connector comprises a 3.5 mm audio socket.

11. The active noise cancelling audio processing device of claim 9, wherein the decoder is operable to receive an audio headset identifier signal via the terminal and to enable or disable decoding of the input signal according to a content of the audio headset identifier signal.

12. The active noise cancelling audio processing device of claim 9, the connector comprising a further terminal for carrying a headphone signal and an identifying signal, and wherein a further output of the decoder is coupled to the further terminal, and the decoder is operable to transmit an identifying signal to a compatible audio headset.

13. An active noise cancellation system comprising:

the audio headset of claim 1 connectable, by their respective connectors, to an active noise cancelling audio processing device including;

a connector for connecting the audio processing device to the audio headset, the connector having a terminal for carrying a microphone signal, an active noise cancelling processor, a decoder having an input coupled to the terminal and an output coupled to the active noise cancelling processor; wherein the audio processing device is operable when connected to an audio headset adapted for active noise cancellation to receive an encoded noise measurement signal from the audio headset via the terminal;

to use the decoder to decode the encoded noise measurement signal; and to use the active noise cancelling processor to generate a combined audio and anti-noise signal; and when connected to an audio headset not adapted for active noise cancelling:

to receive one of an unencoded microphone signal and a null signal from the audio headset via the terminal; and to generate an audio signal not including an anti-noise signal.

14. A mobile phone comprising the active noise cancelling audio processing device of claim 9.

15. An MP3 player comprising the active noise cancelling audio processing device of claim 9.

* * * * *